United States Patent [19]

Adachi

[11] Patent Number: 5,190,916
[45] Date of Patent: Mar. 2, 1993

[54] USE OF OVOMACROGLOBULIN AS AN AGENT FOR TREATING WOUND AND INFLAMMATION

[75] Inventor: Masakazu Adachi, Takasaki, Japan

[73] Assignees: Japan Immuno Research Laboratories Co., Ltd., Takasaki; Otsuka Pharmaceutical Co., Ltd., Tokyo, both of Japan

[21] Appl. No.: 157,508

[22] PCT Filed: Jun. 9, 1987

[86] PCT No.: PCT/JP87/00364
§ 371 Date: Feb. 8, 1988
§ 102(e) Date: Feb. 8, 1988

[87] PCT Pub. No.: WO87/07505
PCT Pub. Date: Dec. 17, 1987

[30] Foreign Application Priority Data

Jun. 13, 1986 [JP] Japan .................. 61-138670
May 29, 1987 [JP] Japan .................. 62-136516

[51] Int. Cl.$^5$ ............... A61K 37/02; A61K 37/10
[52] U.S. Cl. ................................. 514/8; 514/2;
514/21; 514/880; 514/884; 514/886; 514/887
[58] Field of Search ............. 514/8, 2, 21, 844, 880, 514/886, 887

[56] References Cited

U.S. PATENT DOCUMENTS 4,112,074 9/1978 Truffier ........................ 514/21

FOREIGN PATENT DOCUMENTS 2341029 2/1975 Fed. Rep. of Germany .
57-38716 3/1982 Japan .
57-80316 5/1982 Japan .
59-116225 7/1984 Japan .
60-237989 11/1985 Japan .

OTHER PUBLICATIONS

Kitamoto, J. Biochem., 92, 1679–1682 (1982).
Conn's Current Therapy, ed. by R. E. Rankel, M. D., W. B. Saunders Co., 690–691, 1989.
J. Biological Chem., vol. 258, #12, pp. 7481–7489 (1983).
J. Biochem., vol. 92, pp. 1679–1682 (1982).
J. Biochem., vol. 93, pp. 121–127 (1983).

Primary Examiner—F. T. Moezie
Attorney, Agent, or Firm—Oblon, Spivak, McClelland, Maier & Neustadt

[57] ABSTRACT

A treating agent such as a wound therapeutic agent, inflammation therapeutic agent, hair growth agent and hair tonic, and a cosmetic, comprising as an effective component ovomacroglobulin are disclosed. They can act on the skin, a scalp or hairs to exhibit excellent wound curing promotion effect, hair growth promotion effect, and skin or hair protective effect.

6 Claims, 10 Drawing Sheets

USE OF OVOMACROGLOBULIN AS AN AGENT FOR TREATING WOUND AND INFLAMMATION

FIELD OF THE INVENTION

This invention relates to a wound therapeutic agent, trichogen or cosmetic, and more specifically, a wound therapeutic agent, trichogen or cosmetic comprising ovomacroglobulin as its effective component.

TECHNOLOGICAL BACKGROUND

Promoting granulation and epidermarization of a damaged or injured area of the body or a lesion is an important subject in the course of healing a wound such as a general injury, an anal fistula, bedsores, and an incision made in a significant operation extending to a deep portion of the body.

Retinoic acid, allantoin, asiaticoside which is a component of a umbelliferous, zinc, and the lied are known in the art as compounds useful for wound therapeutics. These compounds, however, are not yet satisfactory in the effect of promoting granulation and/or epidermarization. It is also known that the use of a steroid or non-steroid type anti-inflammatory drug for curing ambustions rather decreases the resisting ability of the body, thus requiring the co-use of a medicine which is capable of promoting or generating the resistance.

In the recent past, there have been proposed, as medicines effective for therapy of wounds, a polypeptide comprised of 52 amino acids with an approximate molecular weight of 5300 which is isolated from mammal body fluid (Japanese Patent Laid-Open No. 38716/1982) and a composition comprising essential amino acids (Japanese Patent Laid-Open No. 80316/1982). There is also a prior art publication describing that eggs containing iodine of a concentration of more than 300 μg are effective for promoting a wound healing and preventing occurrence of muscle disorders (Japanese Patent Laid-Open No. 116225/1984. A skin cosmetic composition prepared by incorporating dried egg albumen as a base material has also been proposed (Japanese Patent Laid-Open No. 6801/1986). These compounds or compositions are yet unsatisfactory in their effect for healing a wound. Drugs containing eggs or egg albumen have a problem of a poor storage stability, as they are liable to rot even with antiseptics incorporated therein. Other difficulties in using egg albumen lie in the facts that this compound dissolves only in an alkaline solution, possesses a deficient affinity with other ingredients of cosmetics or ointments which are the conventional application form of a wound therapeutic agent, and tends to produce a white precipitate containing proteins.

They have also been proposed in the art a variety of hair tonics or trichogens which act on hair roots and promote a hair growth. None of these compounds hitherto proposed, however, are yet sufficiently effective.

Furthermore, there has been a need for the development of a cosmetic exhibiting an excellent effect on the skin, protecting it from being roughened, and yet possessing an emolliency (a lubricity-retention performance), a skin-treatment action and a good affinity.

DISCLOSURE OF THE INVENTION

As a result of earnest studies by the present inventors, it was found that ovomacroglobulin exhibits excellent effects on therapy wounds, the hair growth promotion and skin protection, and further that wound therapeutic agents, trichogens such as a hair tonic or hair growth agent, and cosmetics may be obtained by utilizing this compound. Such findings have led to the completion of this invention.

Accordingly, an object of this invention is to provide a wound therapeutic agent, trichogen and cosmetic comprising ovomacroglobulin as an effective component.

Another object of this invention is to provide a method of curing a wound which comprises applying ovomacroglobulin to the wounded area or the lesion.

Another object of this invention is to provide a method of promoting a hair growth which comprises applying ovomacroglobulin to the scalp or hairs.

Still another object of this invention is to provide a method of protecting the skin which comprises applying ovomacroglobulin to the skin.

THE BEST MODE OF CARRYING OUT THE INVENTION

Figure 1:
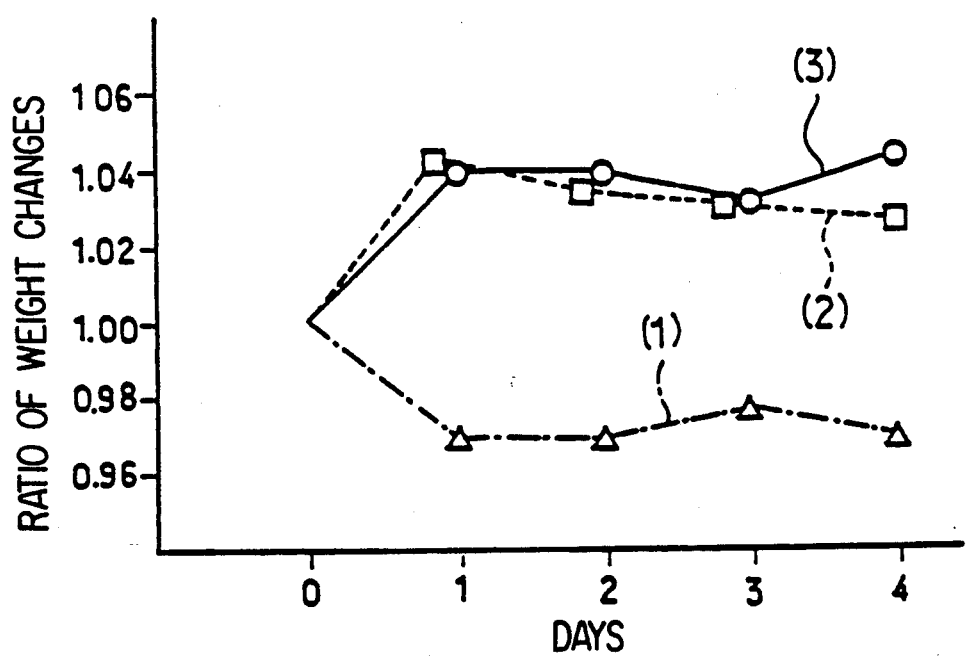
FIG. 1 is a graph showing changes in the body weight of mice which sustained ambustions and subjected to a wound therapeutic test.

The wound therapeutic agents of this invention include the agents for treating or curing external injuries or wounds such as an excoriation, cut, thermal burn, ambustion, congelation, cutis ulcer, chaps, cutis hyperkeratosis, crazing, cracks, dermatitis, dermatomycosis pedis sore, incision, cornea wound and the like; the agents for curing an anal fistula and bedsores; inflammatory treating agents for alveolar pyorrhea, pimples and sunburn; and trichogens including hair-growth promoting agents and hair tonics.

The cosmetics of this invention include skin cosmetics of a variety of forms such as lotion, cream, milky lotion, foundation, as well as various kinds of hair cosmetics to be applied to the scalp or hair such as a shampoo, rinse, hair liquid, set lotion and hair tonic. These cosmetics may be applied on the skin on such instances as after shaving, after the application of a dehairing agent or after the use of a detergent, or may be applied on the roughened skin; and can exhibit the skin protecting or improving effects, provide the skin with wetting or smooth feelings and markedly improve an emolliency, treatment effect and affinity with the skin.

It is essential for the wound therapeutic agent, trichogen and cosmetic of this invention to contain ovomacroglobulin as their active component.

Ovomacroglobulin is known as a sugar protein contained in egg albumen, and the methods of its preparation are also known in the art [Feeney R. E. et al, Comp. Biochem. Physiol., 54A, 281 (1976); Ikari et al, J. Biochem., 92, 1679–1682 (1982), Ibid. 93, 121–127 (1983); and Nagase et al, J.B.C. vol. 258, No. 12, 7481–7489 (1983)].

An application of ovomacroglobulin as an additive to cell culture media is already known in the art (e.g. Japanese Patent Laid-Open No. 237989/1985).

There is no specific limitation on egg albumens to be used as a raw material for preparing ovomacroglobulin. Generally preferably ones may be those of readily available eggs such as eggs of hens, ducks, quails, turkeys and the like, although those of various other animals may also be used. There is also no special limitation on the method for preparing ovomacroglobulin from the egg albumen. Various procedures utilizing the physicochemical properties of ovomacroglobulin may be employed according to the conventionally applied manner for separating components of proteins. These procedures include, for instance, a treatment with a protein precipitant, molecular sieve chromatography (gel filtration), ion-exchange chromatography, centrifugation, electrophoresis, dialysis and the like. They may be used either independently or in combination with other procedures.

One example of the method for preparing ovomacroglobulin from egg albumen comprises first removing insoluble proteins such as ovomucin either by mixing the egg albumen with an aqueous solution such as Tris-HCl buffer or by adding to the egg albumen polyethylene glycol or the like compound, and then subjecting the insoluble protein-free egg albumen to a gel filtration, thus obtaining ovomacroglobulin as a sugar protein with a molecular weight of 600,000 to 800,000.

The wound therapeutic agent of this invention may be prepared by forming its ingredients into conventional dosing forms according to known methods, but for incorporating ovomacroglobulin.

An appropriate dosing form may be selected from among various forms depending on the purpose of use. Such dosing forms may be either, conventional external application forms such as, for example, a fluid coating agent, lotion, aerosol, liniment, ointment and cataplasm, or any other special dosing or application forms like suppository, injection, etc. Various diluents and vehicles may be employed as appropriate in preparing the aforementioned various forms. Taking the preparation of ointments for external applications as an example, conventional hydrophilic or lipophilic base materials, inclusive of fats, fatty oils, lanolin, petrolatum, wax, glycols, higher alcohols, glycerol, water and the like, may be employed. In addition to these base materials various additives known in the art per se, such as a stabilizer, flavoring agent and coloring agent, may also be incorporated as required.

There is no special limitation on the amount of the active component, ovomacroglobulin, to be incorporated in the treating agent of this invention. The specific amount may be determined from a broader range, although it may usually be in a range from 0.0001 to 30 wt %.

The quantity and the method of application of the inventive treating agent can be determined depending on its dosing form, the amount of the active component contained therein, the age, the sex or other conditions of the subject, and the degree or extent of the wound or lesion. In the case of the treating agent of an external application form, for instance, it may be applied, once or several times a day, by dusting or coating it on the lesion in such an amount that the agent may extend over the whole area of the lesion.

A trichogen, in particular, may be applied, for example, on the scalp or hairs.

The inventive cosmetics may be prepared also into various forms as mentioned above, i.e., the forms for the application to the skin such as lotions, creams, milky lotions and foundations, and the forms for the application to the scalp or hairs such as a shampoo, rinse, hair liquid, set lotion and hair tonics. The preparation into these forms may be made according to conventional methods, but for incorporation of ovomacroglobulin into the cosmetic. A variety of the known cosmetics bases as well as various known additives such as a flavoring agent, antioxidant, surface active agent, antiseptics are employed as well.

The amount of ovomacroglobulin to be incorporated into the inventive cosmetic may be determined from a broad range depending on the form, the aimed effect and the like of the cosmetic. It may usually be from 0.0001 to 30 wt %, preferably 0.0001 to 0.1 wt %.

The present invention will now be described in more detail by way of examples and reference examples.

REFERENCE EXAMPLE 1

Preparation of Ovomacroglobulin

Twenty (20) kg of egg albumen was suspended in 10 mM Tris-HCl buffer (pH 7.7) containing the same amount of 1% NaCl. To the suspension was added polyethylene glycol (M.W.=8.500; product of Tokyo Chemicals Co., Ltd.) in such an amount that its concentration become 2.5%. The mixture was subjected to a continuous centrifugation at 10,000 rpm to collect a supernatant, to which was further added the same polyethylene glycol to a concentration of 10%. It was again continuously centrifuged at 10,000 rpm to collect precipitate. The precipitate was dissolved in the same buffer as above, and centrifuged at 10,000 rpm for 10 minutes to collect a supernatant, which was applied to a 252×900 mm Cephalose CL-6B column (Tradename: product of Pharmacia Co.) and eluted with the aforementioned buffer solution at a flow rate of 3.6 liter per hour.

From the eluted fractions, trypsin inhibition active fragments were collected by using the trypsin inhibition activity measurement method based on a casein substrate, proposed by Kitamoto, et al [T. Kitamoto, M.

Nakashima and A. Ikai, J. Biochem., 92, 1979-1682 (1982)].

The active fractions thus obtained were then concentrated by Pelicon cassette (Tradename: manufacture of Millipore Co.) fitted with a 100,000 of molecular sieve membrane, while replacing the buffer with a 5 mM Tris-HCl buffer (pH 7.7). The sample thus obtained was applied to a 50×800 mm DEAE Trisacryl M column (Tradename: product of LBK Co.) which had been equilibrated by a 10 mM Tris-HCl buffer (pH 7.7) added with 10 mM NaCl. After having been thoroughly washed with 10 mM Tris-HCl buffer, the column was eluted by 675 ml of a 10 mM Tris-HCl buffer (pH 7.7) containing 50 mM NaCl for 2.5 hours and 675 ml of a 10 mM Tris-HCl buffer (pH 7.7) containing 150 mM NaCl for 2.5 hours. The trypsin inhibition active fractions were eluted between 70 mM and 120 mM NaCl concentrations under these conditions.

The trypsin inhibition active fractions were collected and dialyzed against a 1 mM phosphate buffer (pH 7.4). After having been thoroughly dialized the dialyzed internal liquid was lyophilized by means of a freeze-dryer (manufactured by Labocorn Co.).

A sample of purified ovomacroglobulin weighing 5.9-7.1 g was obtained by the aforementioned procedures.

The purified sample thus obtained was hydrolyzed in a sealed container under reduced pressure at 110° C. for 24 hours and analyzed by means of an amino acid analyzer (Type 835-50 Hitachi High Performance Amino Acid Analyzer: Tradename, manufactured by Hitachi Ltd.).

The results are shown in Table 1 below.

TABLE 1

| Amino Acid | contents (mole %) |
|---|---|
| Asp | 10.3 |
| Thr | 6.4 |
| Ser | 8.0 |
| Glu | 11.6 |
| Pro | 4.3 |
| Gly | 5.1 |
| Ala | 5.8 |
| Cys/2 | 1.8 |
| Val | 8.2 |
| Met | 2.0 |
| Ile | 6.5 |
| Try | 3.9 |
| Phe | 4.8 |
| Lys | 4.6 |
| His | 1.8 |
| Arg | 3.6 |

EXAMPLE 1

Thermal Burn Vascular Permeability Inhibition Test

The purpose of this test is to evaluate a wound therapeutic effect of the treating agent of this invention, taking as an indicator the vascular permeability of a rat which is determined by quantitation of the amount of a transuded colored substance contained in the body fluid leaching out of the burned lesion of the rat. The rat previously sustained a burn on its skin by means of an electric iron and was given the colored substance (Evans blue).

The test was conducted as follows:

The animals used were 10 Wister male rats weighing 200 to 250 g. The rats were divided into two groups each consisting of 5. Each rat of the groups was hair cut symmetrically along the median line of its back with a hair cutter. A circular thermal burn of a 1 cm diameter was made on the one side of each animal's back by putting on it an electric iron (the temperature on the thermometer scale: 100° to 110° C.) for 20 seconds. The other side of the back was left unburned.

Each rat of the first group was given intradermic injections of a 0.2 ml physiological saline on both burned and unburned sites of its back, immediately after thermal burn and 24 hours thereafter. This group is called the physiological saline administered group or the Control Group. The animals of the other group received intracutaneously in the same manner as above 0.2 ml of an ovomacroglobulin solution of a 10 mg/ml concentration. This group of animals is called the ovomacroglobulin administered group of the Test Group.

At 23.5 hours after the administration of the physiological saline or ovomacroglobulin solution, each rat of both groups was intravenously given 0.5 ml/kg of a 0.5% Evans blue color liquid. At 30 minutes thereafter, i.e., 48 hours after the thermal burn, each rate was bled to death, and each of its burned and unburned skins were stripped off. After removing the fat attached to the skin, it was cut to a 1 cm² square.

The 1 cm² square of the skin was dipped in a 1 ml 1N-KOH aqueous solution, left over for 20 hours at 37° C. to dissolve it in the solution, added with 9 ml of a mixed solution of 0.6 N—$H_3PO_4$ and acetone (5:13), agitated by a mixer, and centrifuged at 3000 rpm and 25° C. to collect a supernatant.

The optical density of the supernatant was measured by a spetrophotometer at a wavelength of 620 nm. The quantity of transuded Evans blue ($\mu$g) was determined from the optical density by using a previously prepared standard curve. The values obtained are designated by a [mean value ± standard error].

The results are shown in Table 2.

TABLE 2

| | Control Group | Tested Group |
|---|---|---|
| Dose (ml/Site) | 0.2 | 0.2 (10 mg/ml) |
| Burned Site | 28.7 ± 5.49 | 16.2 ± 3.82 |
| Unburned Site | 3.6 ± 0.41 | 4.4 ± 0.40 |
| Burned Site-Unburned Site | 25.0 ± 5.32 | 11.8 ± 3.55 |

It is observed from the above table that the transuded Evans blue represented by the value [(Burned Site)—(Unburned Site)] is 25.0±5.32 for the Control Group (the physiological saline administered group), while the corresponding value was 11.8±3.55 for the Test Group (the ovomacroglobulin administered group). These results demonstrate a marked inhibition of the vascular permeability by the administration of ovomacroglobulin.

EXAMPLE 2

Therapeutic Test of Dehairing Cream Induced Skin Inflammation

Twenty (20) Balb/c male mice each weighing 25 to 30 g were used for the test. Hairs on the back of each tested mouse were thoroughly cut with a hair cutter, and 0.5 g of the dehairing cream (Mavi Hair Remover: Tradename, Kanebo Co., Ltd.) were evenly applied to the 2.0×2.5 cm² hair-cut area. Thirty (30) minutes thereafter, the cream was wiped away with warm water, thus preparing the inflammatory skin model.

The mice were divided into 5 groups, 4 for each group, and each mouse of 4 groups were given a test ointment sample as described below on the even day of the inflammation, the next following day, and the 3rd and 6th days, once each day four time in the aggregate, by applying 0.3 g of said ointment on the inflamed site of the skin. Each of these groups are named Test Groups Nos. 1–4.

Test Group No. 1: Japanese Pharmacopoeia hydrophilic ointment (Product of Yoshida Pharmaceutical Co., Ltd.) was applied.

Test Group No. 2: Above ointment added with 0.01% of ovomacroglobulin was applied.

Test Group No. 3: Above ointment added with 0.005% of ovomacroglobulin was applied.

Test Group No. 4: Above ointment added with 0.001% of ovomacroglobulin was applied.

The mice of the remaining one group were left as they were without being treated to observe them as controls (the Control Group).

After application of the ointments macroscopic and histological observations were made every day on the conditions of the skin of each mouse, both of Test and Control Groups. The histological observations were conducted by means of a microscope on the samples stained with hematoxylin and eosin (HE stain).

As a result, it was found that, on the first day of the dehairing treatment, the mice of the Control Group had inflammations in their epidermis and corium, in which inflammatory cells like histiocytes and neutrophil were coagulated, with particularly intense inflammation having been observed in the epidermis and the corium adjacent thereto and substances strongly colored by eosin extending therearound. On the fourth day, it was observed that the tissue image of the epidermis and the corium adjacent thereto had changed to an inflammatory image, and the inflammation had extended over the whole area of the hair follicle.

There were no differences observed between the Test Group 1 (the mice to which hydrophilic ointment was applied) and the Control Group.

In contrast, with regard to the mice of the Test Groups 2–4 the marked inhibition of inflammation in the epidermis, corium and hair follicle was observed, and the tissue image was recognized as having recovered well. It appeared that with respect to the mice of the group to which the ointment with the least ovomacroglobulin concentration were given (Test Group 4), the healing or inhibitive effects were smaller.

Figure 2:
FIG. 2 is a sectional view of the tissue of a model mouse which had received inflammation and was given the inventive treating agent, 8 days after receiving the inflammation.
Figure 3:
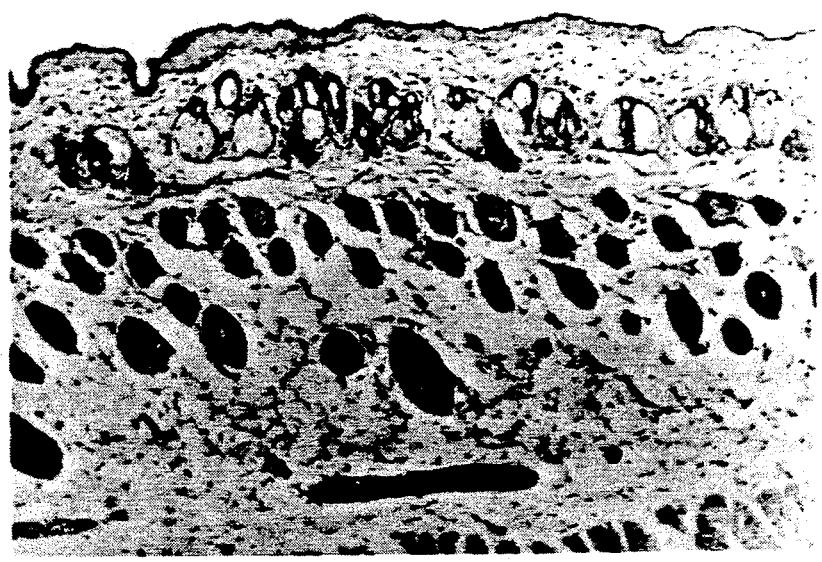
FIG. 3 represents a similar view of the tissue of the control mouse which was given a hydrophilic ointment.

In the histological observation of the Test Group 3 (the mice to which the ointment with a 0.005% ovomacroglobulin concentration was given), on the 8th day following the dehairing treatment, the tissue image was clearer than that observed on the 4th day, and it was confirmed that fresh hair follicles had been growing in the subcutaneous tissue (FIG. 2). The results observed with respect to the Test Group 3 on the 4th day was similar to those of the mice of the Test Group 1, i.e., those given ovomacroglobulin-free hydrophilic ointment (FIG. 3).

It should be noted that the epidermis of a mouse normally takes uneven, rough shape. It was observed on the tested mouse of the Test Groups 2–4 that the healing of lesions had progressed to such an extent that their epidermis had begun to take the above-mentioned normal uneven or rough shape and the cells relating to hair growth had markedly increased and developed, with an early reproduction of hairs having been accompanied therewith (See FIG. 2, for example).

EXAMPLE 3

Thermal Burn Therapeutic Test

Five (5) groups of mice with each group consisting of 4 Balb/c male mice each weighing 25 to 30 g were used for the test.

Hairs on the back of each tested mouse were thoroughly cut with a hair cutter and a dehairing cream was applied on the hair cut skin. After leaving the mouse of 5 minutes (during which inflammation was unlikely to occur), the cream was wiped away with warm water.

Then, a $1.5 \times 2.5$ $cm^2$ area of the hair-cut back of the mouse were burned by applying on it an electric iron (T-27, Paraffin Cutting Fuse Iron: Tradename, product of Takashima Shoten, Japan) at a temperature of 350°–400° C. for 5 minutes.

Beginning from the next following day of the ambustion and on every third day therefrom, the ointments as described below were applied on each tested mouse in the amount of 0.2 g per mouse each time, and the observation on the weight changes as well as both macroscopic and histological observations of the lesions were conducted.

Test Group No. 1: Japanese Pharmacopoeia hydrophilic ointment (Product of Yoshida Pharmaceutical Co., Ltd.) was applied.

Test Group No. 2: Above ointment added with 0.01% of ovomacroglobulin was applied.

Test Group No. 3: Above ointment added with 0.005% of ovomacroglobulin was applied.

Test Group No. 4: Above ointment added with 0.001% of ovomacroglobulin was applied.

The mouse of the remaining one group were left as they were without being treated to observe them as controls (the Control Group).

The results of the body weight changes of the tested mouse are shown in FIG. 1, in which the number of days and the ratio of the weight changes are plotted along the abscissa and ordinate respectively. The Figure shows the weight changes expressed as a ratio of the body weight measured every day after the animals sustained the ambustion (1–4 days in FIG. 1) per the body weight measured on the day of the ambustion (0 day in FIG. 1). In the Figure, a chain line (1) refers to values obtained for Test Group 4 (the group to which ointment containing 0.001% of ovomacroglobulin was given), a dash line (2) refers to those of Test Group 1 (the group to which ovomacroglobulin-free hydrophilic ointment was given) and a solid line (3) refers to those of the Control Group.

The results of the weight changes obtained closely reflect the degree of the ambustion. That is, the body weight increased after animals sustained the ambustion, because progress of the vascular permeability and insensible perspiration caused by local inflammation would produce edemas, which grow larger depending on the size of the area sustained the ambustion.

FIG. 1 clearly shows that there is no indication of the increase in the body weight for Test Group 4, as the growth of edemas was suppressed in animals of this group as compared to the Control Group and Test Group 1, i.e., the group to which ovomacroglobulin-free hydrophilic ointment was given).

Figure 4:
FIG. 4 represents an external appearance of the lesion of a mouse which had received an ambustion and was given the inventive treating agent, 6 days after receiving the ambustion.
Figure 5:
FIG. 5 represents a similar view of the lesion of the control mouse.

As a result of macroscopic observations in the above test it was found that animals belonging to Test Groups 2-4 had markedly recovered from the ambustion as compared with those belonging to the Control Group and Test Group 1. This is also clearly evidenced by the comparison of FIG. 4 (a photograph of the lesion of the Test Group 4 animal on the 6th day of the ambustion) and FIG. 5 (a similar photograph of the control mouse).

Histological observations by means of HE stains were made according to the same manner as in Example 2.

Figure 6:
FIG. 6 represents a sectional view of the tissue of a mouse which had received an ambustion and was given the inventive treating agent, on the 4th day after the ambustion.
Figure 7:
FIG. 7 represents a similar view of the tissue of the control mouse.

The results were that, on the fourth day of the ambustion the mouse from the Control Group and the Test group 1 had the epidermis and corium replaced completely with Eosin stained materials which are characteristic to an ambustion and had the hair follicle only as its shape (See FIG. 7 which is a microscopic photograph on the 4th day of the ambustion of the Control Group). In contrast, the groups to which the inventive wound therapeutic agent were given (e.g. Test Group 3) demonstrated the fact that tissues were in the course of recovery adjacent to subcutaneous tissues of the corium, in which formation of corium-like tissues was starting and hair-roots were favorably growing (See FIG. 6; a microscopic photograph on the 4th day of the ambustion of Test Group 3 to which the ointment containing 0.005% of ovomacroglobulin was given).

It is thus concluded that the edema inhibition effect and the wound therapeutic effect were macroscopically confirmed and further that skin or hair recovery effects, i.e., the tissued formation promoting effects, were histologically recognized.

EXAMPLE 4

Organoleptic Evaluation of the Inventive Cosmetics

A panel of 10 women (age: 25-35) with feelings of roughened skin was selected for the test. Each panelist had the inventive cosmetic (the skin milk of Formulation 1 hereinbelow) applied on her skin twice a day, after leaving bed and before going to bed, for two weeks and upon close of the period answered on three items described below.

As a control test, a control cosmetic sample prepared in the same manner as the above inventive cosmetic, but omitting to incorporate ovomacroglobulin, was evaluated in the same manner as above by 5 female panelists with the similar feeling of roughened skin.

The results of the organoleptic evaluation are shown in Table 3, in which the value (numerator/denominator) indicates (the number of the panelists favorably responded to the evaluated item/total number of the panelists).

TABLE 3

| Items Evaluated | Inventive Cosmetic | Control Cosmetic |
| --- | --- | --- |
| Wetting feeling | 9/10 | 1/5 |
| Smooth feeling | 10/10 | 2/5 |
| Dissolution of skin roughness | 9/10 | 2/5 |

It is evident from the above Table 3 that the inventive cosmetic sample with ovomacroglobulin incorporated therein exhibited excellent results in the organoleptic test.

EXAMPLE 5

Cut Skin Therapeutic Test (1) The back of a rabbit was cut with a silver knife to make 5 thick-split broken wounds, each having a size of 25 mm×25 mm and a depth of 1.2 mm. Each of the wounds were spaced at least by 30 mm so as to eliminate the effect of wound curing mechanism between them.

Each one of the medicines (A) to (D) described below was applied on each wound once a day, leaving one remaining wound without any treatment so as to evaluate it as a control. After the application the wounds were covered by gauze (size: 25 mm×25 mm), sealed by air permeable nylon film (Tegadam: Registered Tradename, Three M Ltd.) so as to avoid contamination with other medicines, and whole area of the wounds was sealed by an elastic bandage. These treatments were followed over the whole period of the observations.

| [Medicines] | |
| --- | --- |
| (A) Hydrophilic petrolatum ointment | |
| Bleached bees wax | 8 g |
| Stearyl alcohol | 3 g |
| Cholesterol | 3 g |
| White petrolatum | 86 g |
| Propyl paraben | 0.0625 g |
| | (100 g) |
| (B) Hydrophilic petrolatum ointment containing 1% of ovomacroglobulin | |
| 5% ovomacroglobulin aqueous solution (containing 40 mg of methyl paraben) | 20 g |
| Hydrophilic petrolatum base material | 80 g |
| (C) Hydrophilic petrolatum ointment containing 0.1% of ovomacroglobulin | |
| 0.5% ovomacroglobulin aqueous solution (containing 40 mg of methyl paraben) | 20 g |
| Hydrophilic petrolatum base material | 80 g |
| (D) Hydrophilic petrolatum ointment containing 0.01% of ovomacroglobulin | |
| 0.05% ovomacroglobulin aqueous solution (containing 40 mg of methyl paraben) | 20 g |
| Hydrophilic petrolatum base material | 80 g |

(2) evaluation of the wound therapeutics was carried out by the observations of following items immediately after wound, and 7, 24 and 21 days thereafter.

(A) Epithelialization of the Wound

Progress of healing was evaluated by taking photographs at each observation.

(B) Histological Observations

A wounded phase was inspected, and the amount of collagen fibers, its morphology in granulation tissues, and the formed epithelium were observed with respect to HE stained specimen.

(C) Evaluation of Side Effects

Presence or absence of the stimulation to a normal skin (turning to red) and skin inflammation were observed.

RESULTS

Figure 8:
FIGS. 8 and 9 each represents an external appearance of the lesion of a rabbit which had sustained peeling of its skin and was given the inventive treating agent, on the 7th day of peeling.
Figure 9:
Figure 10:
FIG. 10 represents a similar view of the lesion of the control rabbit.
Figure 11:
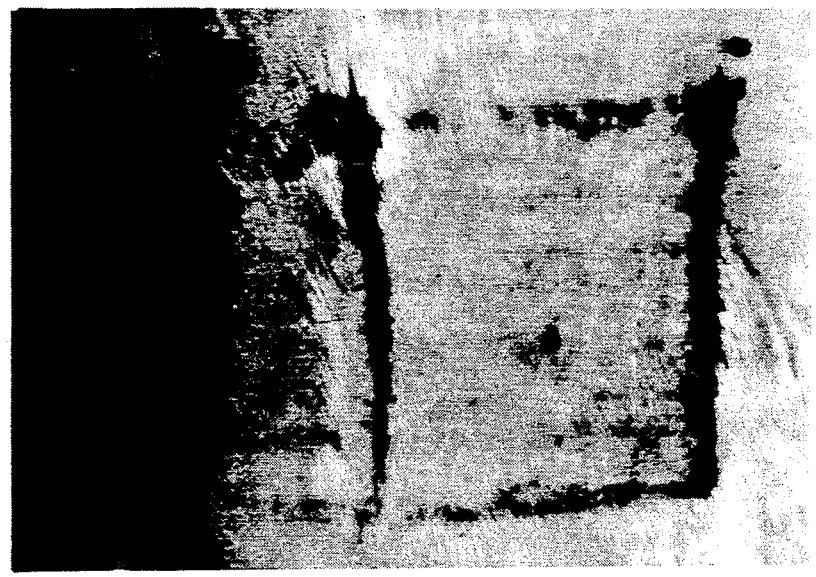
FIGS. 11 and 12 each represent an external appearance of the lesion of a rabbit which had its skin peeled off and was given the inventive treating agent, on the 21st day of the peeling.
Figure 12:
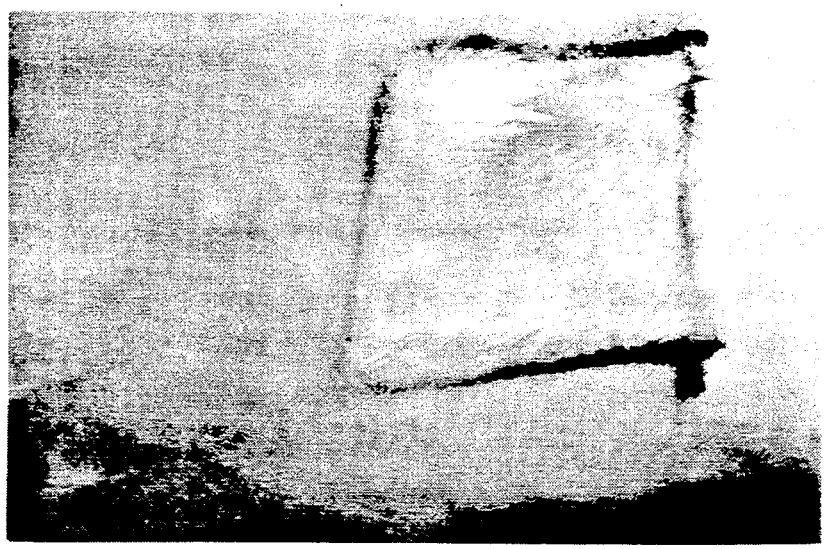
Figure 13:
FIG. 13 represents a similar view of the lesion of the control rabbit.

In the above experiment, on the 7th day following the wound preparation, the size of the wounds to which ointments containing 0.01% and 0.1% of ovomacroglobulin were applied were slightly smaller (See FIGS. 8 and 9) than that to which the hydrophilic ointment was applied (See FIG. 10) and the histological observations revealed the formation of granulation tissues. There was observed further progress in the wound therapeutic effects of ovomacroglobulin on the 14th day, that is, the observed size of the wounds to which the ointments containing 0.01% and 0.1% of ovomacroglobulin were given were markedly smaller than that applied with the hydrophilic ointment. The differences between them were apparent in the histological observations as well, in terms of the formation of granulation tissues, the amount of collagen and growth of epithelium tissues. The observation on the 21st day following the wound preparation revealed the marked shortened period for the healing of the sites to which the 0.01% and 0.1% ovomacroglobulin content ointments were applied (FIGS. 11 and 12) over those to which hydrophilic petrolatum was applied (FIG. 13). The effect was similarly observed by the histological observations, i.e., the granulation, the increase in collagen fibers and the growth of epithelium cells were remarkable. As another experiment, an ovomacroglobulin ointment was applied to a normal skin to observe its side effect. As a result, neither red spots on the skin nor any incidence of dermatitis were recognized.

The experiment using the ointment with a 1.0% ovomacroglobulin content gave the similar results as that using the ointment with a 0.1% ovomacroglobulin content.

EXAMPLE 6

Extension Test on Cornea Epitherial Cells

A rabbit weighing 2.5 g to 3.0 kg was anesthetized by way of intravenous administration of pentobarbital (product of Pitman-Moor Co.) in an amount of 30 mg/kg. The cornea was then extracted and made into 2×4 mm strips of cornea pieces.

The cornea pieces thus obtained were cultured for 28 hours in TC-199 culture solutions to which ovomacroglobulin was dissolved to concentrations of 0.05 μg/ml, 0.5 μg/ml and 5 μg/ml. After having been cultured, the tissue pieces were fixed by a mixed solution of 5% glacial acetic acid and 95% ethanol and embedded into paraffin, from which 4 μm cut pieces were prepared. These pieces were subjected to a conventional HE stains and the length of the extended cornea epithelial cells were measured by the observation using a microscope.

Figure 14:
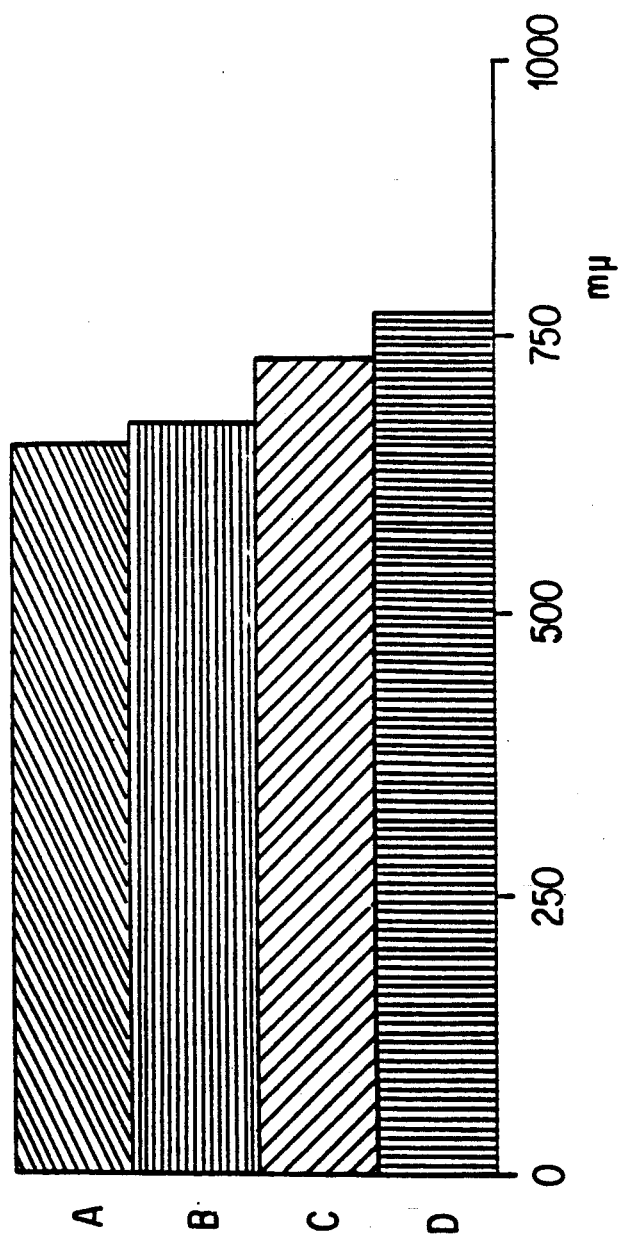
FIG. 14 is a graph showing the development of cornea epithelial cells.

As a result, it was found that ovomacroglobulin promoted the extension of cornea epithelial cells dose dependently as shown in FIG. 14, in which A indicates the controls, the TC-199 culture solution, and B, C and D indicate the same culture solutions to which 0.05 μg/ml, 0.5 μg/ml and 5 μg/ml of ovomacroglobulin were added, respectively.

EXAMPLE 7

Parodontium Wound Therapeutic Test

Wounds were formed on parodontiums of rats according to the following methods 1 and 2 in order to study the therapeutic action of the inventive testing agent.

PREPARATION OF WOUNDS

1. A hooked probe was inserted around the center of the right and left upper posterior teeth from the palate side of a rat (age: 12 weeks). After the probe reached the born, it was reciprocated several times along the crown to form a wound. Thereafter, a root canal therapy K file No. 40 was inserted just under the contact point of the right second posterior tooth thus making a path between the cheek side and the palate side. A silk thread (blade silk) 4-0 was wound once around the second posterior tooth and knotted on the cheek side. After confirming hemostasis, the test paste was applied. All of these procedures were carried out under abdominal anesthesia using Ketaral.

2. Removal of the gingiva was conducted by making an incision from the efferent of the third posterior tooth through the mesial of the first posterior tooth using 190 12 bird beak blade scissors, and inserting and reciprocating a hooked probe therethrough. A bone phase was exposed for approximately 0.5 mm.

| (Test Paste) | |
|---|---|
| (A) Control Paste | |
| Hydrophilic petrolatum paste* | 100 g |
| (B) Paste with a 0.005% ovomacroglobulin content | |
| 0.025% ovomacroglobulin aqueous solution (containing 40 mg of methyl paraben) | 20 g |
| Hydrophilic petrolatum* | 80 g |
| (C) Paste with a 0.1% ovomacroglobulin content | |
| 0.5% ovomacroglobulin aqueous solution (containing 40 mg of methyl paraben) | 20 g |
| Hydrophilic petrolatum* | 80 g |
| *Composition of hydrophilic petrolatum (per 100 g) | |
| Bleached bees wax | 8 g |
| Stearyl alcohol | 3 g |
| Cholesterol | 3 g |
| White petrolatum | 86 g |
| Propyl paraben | 0.0625 g |

The Method of Administrator

Each of the above pastes was put on a tray and applied to a rat once a day, for 15 minutes each time, in an amount of approximately 0.32 g in average. The first application was given after confirming the hemostasis, and the animals were not given drinking water for 2 hours after the application. The above procedures were conducted under abdominal anesthesia of Nembutal (0.1 ml).

Evaluation

The treated rats were killed on the first day following start of the experiment, and the 2nd and 7th days. The lesions were taken out, fixed by Bouin fixative, decalcified with trichloroacetic acid, embedded in paraffin, stained by HE or azan, and subjected to observation for inspecting the number of inflamed cells and changes in collagen fibers.

Results

The therapeutic effects of the inventive wound therapeutic agent on the next following day of the wound preparation and the application of the inventive agent thereto, in terms of humectation of inflammatory cells, the state of hemorrhage in the tissues, and the state of collagen fibers were as follows:

(1) HUMECTATION OF INFLAMMATORY CELLS AND THE STATE OF HEMORRHAGE IN TISSUES

Figure 15:
FIG. 15 represents a sectional view of the parodontium of a mouse which had received a wound and was given the inventive treating agent, on the 7th day of the wound.
Figure 16:
FIG. 16 represents a similar view of the control mouse.

Observation of the control revealed the fact that there were intense capillarectasias and hemorrhage images in the area of the gingival lamina proria extending from the gingival crevice epithelium through the top of the alveolar bone, with the humectant fibrin horizon and scattered neutrophil surrounding said area (FIG. 16). On the other hand, in the wounds to which the inventive external agent was given the state of hemorrhage was not so intense and the lamina proria appeared to have already been covered by the fibrin horizon, although there were observed capillarectasias in the lamina proria. The humectation of the lamina proria neutrophils was less than the controls, though the intense localized images of humectant neutrophils were observed on the gingival crevice epithelium and the fibrin horizon surface of the junctional epithelium. When the groups applied with the pastes with 0.005% and 0.1% ovomacroglobulin content were compared, the latter had less capillarectasias and hemorrhage images in the lamina proria and appeared to have less humectant neutrophils in the epithelium than the former. Shown in FIG. 15 is a photograph of a cross section of the tissue to which the paste with a 0.005% ovomacroglobulin content was given.

(2) STATE OF COLLAGEN FIBERS

The coloration of collagen fibers was made by means of the axan stain. Using HE stain there were observed plasmotomies, alterations and the like in collagen fibers in the vicinity and around the wound of the control, while in the wound samples to which the inventive external agent was given the plasmotomy of collagen fibers seemed not to have extended to around the wound although there were the plasmotomies in its close vicinity. The tendency was more intense in the group given the paste with a 0.1% ovomacroglobulin content than that given the paste with a 0.005% ovomacroglobulin content.

EXAMPLE 8

Given below exemplarily are the formulations of the inventive treating agents. In the following formulations figures for various ingredients designate "part(s) by weight".

| Formulation 1: Inventive Cosmetic Preparation of skin milk | |
|---|---|
| Liquid paraffin (100–110 cp) | 7 |
| Cetyl alcohol | 0.5 |
| 85% glycerol | 7 |
| Ovomacroglobulin | 0.01 |
| Dimethylaminopropyl lanolin acid amide disulphate | 0.03 |
| Antiseptics (methyl paraben) | 0.2 |
| Flavoring agent | appropriate amount |
| Water | balance |
| | 100 |

A homogeneous mixture was prepared by first mixing ovomacroglobulin, dimethylaminopropyl lanolin acid amide disulphate and glycerol, and subsequently adding water while stirring at 75° C. Another homogeneous mixture was prepared by mixing liquid paraffin, cetyl alcohol and methyl paraben under stirring and heating at 75° C. Then, the former mixture was added gradually to the latter while the latter was stirred and kept at the temperature of 75° C. After the addition the mixture was left over to cool down to room temperature, and the flavoring agent was added to obtain the skin milk of this invention.

| Formulation 2: Inventive Cosmetic Preparation of skin cream | |
|---|---|
| Liquid paraffin (100–110 cp) | 5 |
| Isopropylmyristate | 10 |
| Stearic acid | 3 |
| Cetanol | 2 |
| 85% glycerol | 10 |
| Polyoxyethylene (EO = 4) stearate | 1 |

| -continued | |
|---|---|
| Formulation 2: Inventive Cosmetic Preparation of skin cream | |
| Ovomacroglobulin | 0.001 |
| Dimethylaminopropyl lanolin acid amide disulphate | 0.04 |
| Antiseptics (methyl paraben) | 0.2 |
| Flavoring agent | appropriate amount |
| Water | balance |
| | 100 |

The inventive skin cream was prepared based on the above formulation and according to the same manner as in the above skin milk of the Formulation 1.

| Formulation 3: Inventive Cosmetic Preparation of skin lotion | |
|---|---|
| 95% ethyl alcohol | 20 |
| 85% glycerol | 5 |
| Polyoxyethylene (EO = 20) sorbitan lanolin acid monoester | 0.5 |
| Ovomacroglobulin | 0.005 |
| dimethylaminopropyl lanolin acid amide disulphate | 0.04 |
| Antiseptics (methyl paraben) | 0.2 |
| Flavoring agent and coloring agent | appropriate amount |
| Water | balance |
| | 100 |

A homogeneous mixture was prepared by first thoroughly mixing ovomacroglobulin, dimethylaminopropyl lanolin acid amide disulphate and glycerol, and subsequently adding water while stirring. Another homogeneous mixture was prepared by dissolving the flavoring and coloring agents and the antiseptics in ethyl alcohol, followed by the addition the former mixture was added to the later while stirring and then filtered to obtain the skin lotion of this invention.

Formulation 4: Inventive Cosmetic

Preparation of a skin lotion

The skin lotion was prepared according to the same formulation and in the same manner as the above skin lotion of the Formulation 3, except that the amount of ovomacroglobulin added was 0.0001 part by weight in this Formulation 4.

| Formulation 4: Inventive Treating Agent | |
|---|---|
| Ovomacroglobulin | 0.01 g |
| Antiseptic | appropriate amount |
| Flavoring agent | appropriate amount |
| Distilled water | balance |
| | 100 ml |

Distilled water was added to ovomacroglobulin, the antiseptics and the flavoring agent to make the whole volume to 100 ml. After sterilization the solution was made into a spraying type to obtain the wound therapeutic agent of this invention.

| Formulation 6: Inventive Treating Agent | |
|---|---|
| Obomacroglobulin | 0.05 g |
| Antiseptics | appropriate amount |
| Flavoring agent | appropriate amount |

| Formulation 6: Inventive Treating Agent | |
| --- | --- |
| Distilled water | balance |
| | 100 ml |

A spraying solution type inventive treating agent was prepared based on the above formulation and in the same manner as the above preparation of the inventive treating agent of the Formulation 5.

| Formulation 7: Inventive Treating Agent Preparation of a hydrophilic ointment | |
| --- | --- |
| Obomacroglobulin | 0.5 g |
| White petrolatum | 250 g |
| Stearyl alcohol | 220 g |
| Propylene glycol | 120 g |
| Sodium lauryl sulfate | 15 g |
| Ethyl (or methyl) p-oxybenzoate | 0.25 g |
| Propyl p-oxybenzoate | 0.15 g |
| Purified water | appropriate amount |
| | 1000 g |

An inventive treating agent containing ovomacroglobulin of a hydrophilic ointment form was prepared according to the above formulation.

Formulations 8-11: Inventive Treating Agents

Inventive treating agents were prepared according to the above Formulation 7, except that the amounts of ovomacroglobulin formulated to Formulations 8, 9, 10 and 11 were 0.01 g, 0.05 g, 0.1 g and 1 g, respectively.

INDUSTRIAL UTILIZATION

The treating agent of this invention prepared as illustrated above, when applied as a wound therapeutic agent, exhibits an excellent wound curing promotion effect which is far superior to other various wound therapeutic agents or methods.

When the agent is used as a trichogen, it can not only exhibit hair growth promotion effect but also provide hair protecting or improving effect. These effects may give rise, for example, to a dissolution of roughened hairs and improvement in hair gloss.

Further, when the agent is used as a cosmetic it can exhibit the protective or improving effects on the skin or hairs, and has various advantages over other cosmetics of this kind.

The inventive treating agents or cosmetics also have excellent storage stability and safety.

I claim:

1. A method of treating a wound in a patient, comprising administering an effective amount of ovomacroglobulin, to said patient in need of the treatment.

2. The method of claim 1, wherein said wound is selected from the group consisting of an excoriation, a cut, a thermal burn, an ambustion, a congelation, cutis ulcer, chaps, cutis hyperkeratosis, crazing, cracks, dermatitis, dermatomycosis, pedis sore, incision, cornea wound, anal fistula, and bed sores.

3. The method of claim 2, wherein said wound is a thermal burn or an ambustion.

4. The method of claim 2, wherein said wound is a cornea wound.

5. A method of treating inflammation in a patient, comprising administering an effective amount of ovomacroglobulin to said patient in need of the treatment.

6. The method of claim 5, wherein said inflammation is an alveolar pyorrhea.

* * * * *